United States Patent
Jaffe

(12) 
(10) Patent No.: US 6,620,798 B1
(45) Date of Patent: Sep. 16, 2003

(54) SYNERGISTIC AGENTS FOR ENHANCING TISSUE REPAIR

(76) Inventor: Russell Jaffe, 10430 Hunter View, Vienna, VA (US) 22181

( * ) Notice: Subject to any disclaimer, the term of this patent is extended or adjusted under 35 U.S.C. 154(b) by 0 days.

(21) Appl. No.: 09/588,677

(22) Filed: Jun. 6, 2000

(51) Int. Cl.$^7$ .................. A01N 43/04; A01N 59/26; A61K 31/70; A61K 33/42

(52) U.S. Cl. ................. 514/62; 514/2; 514/8; 514/54; 514/453; 514/456; 514/476; 514/579; 424/601; 424/605; 424/606

(58) Field of Search ............... 514/62, 54, 476, 514/579, 456, 453, 2, 8; 424/605, 601, 606

(56) References Cited

U.S. PATENT DOCUMENTS

| | | | |
|---|---|---|---|
| 5,626,883 A | * 5/1997 | Paul | 424/605 |
| 5,650,433 A | * 7/1997 | Watanabe et al. | 514/456 |
| 6,203,818 B1 | * 3/2001 | Vester | 424/464 |
| 6,333,304 B1 | * 12/2001 | Bath et al. | 514/2 |

OTHER PUBLICATIONS

Deal et al. (Rheumatic Diseases Clinics of North America (May 1999) 25(2): 379–395).*

NCBI MeSH Browser—Musculoskeletal System (http://www.ncbi.nlm.nih.gov:80/entrez/meshbrowser.cgi?term=Musculoskeletal+System&retrievestring=&mbdetail=n).*

NCBI MeSH Browser—Myocardium (http://www.ncbi.nlm.nih.gov:80/entrez/meshbrowser.cgi?term=Myocardium&retrievestring=&mbdetail=n).*

* cited by examiner

*Primary Examiner*—Kenneth R. Horlick
*Assistant Examiner*—Alexander H. Spiegler
(74) *Attorney, Agent, or Firm*—Morrison & Foerster, LLP

(57) ABSTRACT

Methods for the repair, reconstruction and protection of tissue using compositions containing flavonoids and/or flavonols, including simultaneous administration of agents in order to obtain synergistic effects from the combinations taught and claimed herein. The administration of the flavonols and /or flavonoids in conjuction with compositions containing vitamin C and/or salts and esters of vitamin C provides advantageous sparing of autocoids (internal steroids). The simultaneous administration of flavonols and /or flavonoids to compositions containing glucosamine and or glucosamine sulfate and chondroitin stimulates rapid improvement in joint function. The addition to the flavonoids and/or flavonols to previously administered compositions is a most convenient method of achieving enhanced benefits. The use of combinations of flavonoids and flavonols for use in relieving pain is also a part of the invention.

10 Claims, No Drawings

SYNERGISTIC AGENTS FOR ENHANCING TISSUE REPAIR

FIELD OF THE INVENTION

This invention is related to the repair, reconstruction and protection of tissue using compositions containing flavonoids and/or flavonols.

BACKGROUND OF THE INVENTION

It has been known that phenolic compounds, including flavonoids and flavonols, have anti-inflammatory properties. It has been known that several flavonones, flavonols, isoflavonones and catechins, can inhibit the proliferation of inflammatory (granulation) tissue. These agents can decrease capillary permeability and strengthen the blood vessel wall, thus preventing vascular fragility. The agents have been shown to have affinity for and enhance synthesis of connective tissue.

Some flavonoids have been found to stimulate collagen and elastin cross-linking. It is believed that proline hydroxylation and modulation of polysaccharide production and function may be among the mechanisms by which benefit occurs. However, bioaction of these compounds, when given alone, is inadequate to provide desired clinical results. It is necessary to find more effective means of delivering clinical benefits that can arise from exposure to flavonoids.

Glucosamine and/or glucosamine sulfate used in conjunction with chondroitin have been used previously to treat diseases arising from pathological changes (for example, osteoarthritis) in joints for purposes of reducing pain and increasing mobility. Clinical improvement in motion and reduction of pain are reported. However, the time required to achieve reduction in pain is measured in months and the improvement in mobility is usually modest. For example, four to sixteen weeks is usually needed before measurable reduction in pain is observed. Mobility improvements in the range of only 1:5 to twenty-five degrees are achieved. While such improvement is helpful, the long period of time required to achieve benefit results in voluntary ceasation of treatment in many patients. There is need for means of treatment that will provide noticeable improvement in joint comfort and function in a shorter time period.

Ascorbic acid (vitamin C), its salts and esters (hereinafter often referred to as ascorbate), have frequently been used to augment the vitamin C usually found in the diet. Ascorbates have been known to be essential to collagen formation and to maintenance of the integrity of structures of mesenchymal origin. Ascorbates have been given both systemically and topically to enhance wound healing and are necessary for utilization of folate, a B vitamin. Vitamin C facilitates absorption of iron and is necessary to the utilization of folic acid ingested in the diet. Potassium, calcium, magnesium and/or zinc ascorbates are useful reducing substances that stimulate connective tissue synthesis, have steroid-sparing effects, and act as biological reducing agents. Thereby, ascorbate enhances detoxification of a variety of environmental toxins from nitrosamines to chlorinated heterocyclic pseudoestrogens. There is a need for properly balanced ascorbate forms which can provide improved benefit.

SUMMARY OF THE INVENTION

It is the purpose of this invention to provide increased benefit from known agents by providing simultaneous administration of agents, which have previously been given separately for differing purposes, in order to obtain synergistic effects from the combinations taught and claimed herein. The administration of flavonols and/or flavonoids in conjunction with compositions containing vitamin C and/or salts and esters of vitamin C provides advantageous sparing of autocoids (internal steroids). The simultaneous administration of flavonols and/or flavonoids to compositions containing glucosamine and or glucosamine sulfate and chondroitin stimulates rapid improvement in joint function. The addition to the flavonoids and/or flavonols to previously administered compositions is a most convenient method of achieving enhanced benefits.

The use of combinations of flavonoids and flavonols for use in relieving pain is also a part of the invention. The reliance on flavonoids and flavonols for relief of pain whilst avoiding use of non-sterolidal anti-inflammatory drugs (NSAIDs) was not previously considered.

DETAILED DESCRIPTION OF THE INVENTION

Administration of compositions containing glucosamine and/or glucosamine sulfate and chondroitin in conjunction with flavonols and/or flavonoids provides decrease in discomfort and increase in mobilitylin patients with degenerative joint conditions. Such improvement is not seen when only the glucosamine and/or glucosamine sulfate and chondroitin are administered or when only flavonoids in combination with flavonols is given. As seen in Example 1, the combination of the invention offers much improved treatment modality to patients suffering from degenerative processes such as osteoarthritis/osteoarthrosis.

When the cause of discomfort results from trauma to otherwise healthy tissue, it is appropriate to administration of flavonoid/flavonol compositions (without glucosamine/glucosamine sulfate) to relieve the pain and inflammation. The pain reduction afforded by the combination is comparable to or better than that achieved with non-steroidal anti-inflammatory drugs (NSAIDs). It has also been noted that the addition of manganese (specifically) appears to further increase the benefit afforded from the compositions, as is exemplified below. It was not previously known that the use of flavonoid/flavonol compositions could be relied on for relief of pain.

MATERIALS AND METHODS

The flavonols and flavonoids are available from many natural sources. Those exemplified in the compositions were obtained from Ashland Chemical Company, Ashland, Oreg. The flavonols used in the particular examples were extracted from pine bark or grape seeds. The flavonoids were extracted from *S. japonica*.

The balanced potassium, calcium, magnesium and zinc ascorbates are prepared by reacting the respective potassium, calcium, magnesium and zinc soluble carbonates with ascorbic acid. (The ascorbic acid was obtained from Takeda, Inc and Merck.

The glucosamine and glucosamine sulfate are available from Seltzer Chemical Co or ZetaPharm, Inc.

EXAMPLE 1

Glucosamine, chondroitin, flavonol and flavonoid composition

An 84 year old male with a long history of osteoarthritis was found to have a left knee joint mobility of <15 degrees.

After six months of intensive therapy with glucosamine (1500 mg), glucosamine sulfate (1500 mg) chondroitin (1200 mg) his pain was deemed reduced by about 10% and his joint mobility had increased by 5 degrees to 20 degrees.

In accord with the claims of this invention, the regimen described above was replaced with the following combination:

| | |
|---|---|
| glucosamine: | 900 mg |
| glucosamine sulfate: | 300 mg |
| chondroitin: | 250 mg |
| quercitin dihydrate flavonoid | 1500 mg |
| OPC flavonols | 15 mg |
| manganese | 50 mg | along with usual appropriate diet and exercise regimen. Within six weeks, his pain was markedly reduced (about 95%) and his joint mobility increased to 90 degrees (within the healthy range for non-osteoarthritic individuals).

In view of the above, it was postulated that the 'repair plateau' seen with the prior regimen was due to lack of stimulation of internal structural matrix necessary for more complete repair. the provision of cartilage building blocks (glucosamine and/or glucosamine sulfate in the range of 250–2500 mg per day, and chondroitin in the range of 250 to 2500 mg do not stimulate internal matrix structural formation. It is believed the unexpected results arising from inclusion of flavonoid and/or flavonol given in combination with the glucosamines and chondroitin result in synergism that provides the unexpected benefits described above.

In a preferred embodiment, quercitin, particularly free quercitins such as quercitin dihydrate (a flavonoid) and orthoproanthocyanidins (OPC) (a flavonol), working in synergy, stimulate matrix elements to provide the superior results. A particularly preferred flavonoid/flavonol ratio is quercitin flavonoid to flavonol (for example, OPC) ratio of 100:1. Addition of some minerals such as manganese at a dosage of 1–1000 mg is beneficial for production of superior results. Pain reduction in patients whose discomfort arises from degenerative processes begins to be noted within 1.5–5 weeks and joint mobility improvement of >35 degrees (typically ≧70 degrees) can be expected using the combination of the invention.

The combination of flavonoids and flavonols to provide pain relief is important, since neither the flavonoids nor the flavonols alone give adequate relief, even when one active agent is given at five times the dosage provided in the combination. That the flavonoid/flavonol compositions can be used without NSAID's in patients suffering from trauma to the musculoskeletal system was not previously known.

EXAMPLE 2

Use of flavonoid/flavonol combinations for acceleration of tissue repair and reduction of pain A preparation containing 2000 mg of quercitin and 20 mg OPC flavonols was given to one group of patients every 6 hours relief of pain. A second group of patients were given 650 mg of NSAID (CELEBRIX™) every 4 hours.

| Condition | NSAID effect | Flavonoid/flavonol/effect |
|---|---|---|
| Acute knee trauma patellar dislocation | pain dec = 5 mobility = 10 | pain dec = 85 mobility = 85 |
| Blunt injury to R. shoulder | pain dec = 20 mobility = 25 | pain dec = 100 mobility = 100 |
| Basketball "groin muscle pull" | pain dec = 15 mobility = 30 | pain dec = 95 mobility = 100 |

Neither flavonoids nor flavonols alone, even at 5 time the levels reported in the above, resulted in appreciable decrease in pain or increase in mobility.

Flavonols in combination with vitamin C, its salts and/or esters (herein, called ascorbates) provide other valuable synergistic effects. The body, when functioning properly, automatically produces steroids in appropriate amounts. However, under pathological conditions the body can overproduce steroids. Furthermore, the use of exogenous steroid therapy for treatment often results in inappropriate levels of steroid in the body. One result of excess levels of steroids, whether as a result of excess production by the body or as a result of exogenous administration, is damage to connective tissue. Vitamin C and its analogues has been previously given to assist the body in regulation of steroids in the body. The dosage requirements of the individual can be determined based on amounts of buffered ascorbate necessary to saturate tissues and generate an abundant aqueous fluid production in the terminal colon and rectum. This fluid production is sometimes known as an 'ascorbate flush' or a 'C flush'. This is the first non-invasive method for determining individual ascorbate needs. It has now been clinically determined that 75% of the amount needed to achieve a 'C flush' is the amount needed throughout the day to provide sufficient ascorbate intake to facilitate beneficial steroid balancing effect on the body.

Potassium, calcium, magnesium and/or zinc ascorbate are effective in rebuilding cellular and systemic ascorbate pools, thus enhancing: detoxification, restoring a healthy, low oxidation/reduction potential and stimulating tissue structural and functional protein, glycoprotein and lipoprotein synthesis, while reducing endogenous or exogenous steroid need. In addition, ascorbate is a preferred antioxidant for quenching all water-soluble free radical oxidation reactions. Further, ascorbate accelerates toxic minerals (e.g., lead, mercury, cadmium, nickel and arsenic) excretion in the urine and stool. There is need for compositions containing properly balanced ascorbate forms which resolve existing defects in forms previously available to provide improved a scorbate dosing.

EXAMPLE 3

Compositions containing salts of ascorbic acid

The correct combination of active agents for purposes of enhancing appropriate steroid balancing in the body is 0.5 to 1500 mg/day of flavonols, (preferably about 10 mg/day for an adult), 5–15,000 mg per day of flavonoids (preferably about 1000 mg/day for an adult) and a mixture of salts of ascorbic acid. The preferred salts of ascorbic acid are potassium (50–500 mg/day), calcium (10–250 mg/day) magnesium (10–250 mg/day) and zinc (0.1 to 10 mg/day) salts of the acid. A preferred regimen provides the following amounts per day for a adult:

| | |
|---|---|
| OPC | 10 mg |
| quercitin dihydrate | 1000 mg |
| potassium ascorbate | 60 mg/gm |
| Calcium ascorbate | 40 mg/gm |
| Magnesium ascorbate | 20 mg/gm |
| zinc ascorbate | 0.4 mg/gm |

Such balanced ascorbate salts enhance the anti-oxidant activity, promote toxic mineral excretion, enhance production and utilization of functional proteins and structural matrix elements.

The amount of ascorbate needed is determined using the 'ascorbate flush' or 'C flush method. A buffered ascorbate solution (containing potassium, calcium, magnesium and zinc) is prepared by dissolving ascorbate powder in 1–2 ounces of water or juice. The appropriate amount, for a healthy person being about ½ teaspoon every 15 minutes in 1–2 ounces of liquid, for a moderately healthy person, 1 teaspoon every 15 minutes and for a person that is ill, about 2 teaspoons every 15 minutes. The ascorbate may be prepared by dissolving 40 grams of the ascorbate in 10–20 ounces of liquid, then placed in a sealed bottle to avoid oxidation.

After dissolving the ascorbate, allow any effervescence to abate (about 2 minutes) take the suggested amount of the solution until watery diarrhea occurs. A flush should be reached before going to bed. Calculate the total amount of ascorbate consumed, 75% of this total is the approximate daily need for vitamin C for that individual at that time. This is a non-invasive clinical method for assessing the consumption rate or biological half-life of ascorbate in vivo. As sufficient vitamin C accumulates in the body, less ascorbate is needed. The appearance of watery stool indicates that less ascorbate is needed. The flush can be repeated to determine appropriate dosage of ascorbate.

What is claimed is:

1. A method of treating osteoarthritis comprising administering a composition of matter containing joint-protecting effective amounts of glucosamine and/or glucosamine and chondroitin in conjunction with 5–15,000 mg/day of flavonoid(s) and 0.5 to 1,500 mg/day of flavonol(s).

2. The method of claim 1 wherein the flavonoid:flavonol ratio is about 100:1.

3. The method of claim 1 wherein the flavonoid administered is quercitin dihydrate.

4. The method of claim 2 wherein the flavonoid administered is quercitin dihydrate.

5. The method of claim 1 wherein the flavonol administered is an orthoproanthocyanidin.

6. The method of claim 2 wherein the flavonol administered is an orthoproanthocyanidin.

7. A composition of matter comprising a joint-protecting effective amount of glucosamine and glucosamine sulfate, 5–15,000 mg of flavonoid(s) and of 0.5–1,500 mg of flavonol(s).

8. A method of dosing a mammal, comprising administering a composition comprising at least one flavonoid and at least one flavonol, 50 to 500 mg potassium ascorbate, 10–250 mg calcium ascorbate, 10–250 mg magnesium ascorbate, and 0.1 to 10 mg zinc ascorbate, wherein the ratio of flavonoid to flavonol is about 100:1.

9. A composition of claim 7 containing, additionally, 1–1000 mg manganese.

10. A composition comprising flavonoid and flavonol in a ratio of about 100:1, 50 to 500 mg potassium ascorbate, 10–250 mg calcium ascorbate, 10–250 mg magnesium ascorbate and 1 to 10 mg zinc ascorbate.

* * * * *

UNITED STATES PATENT AND TRADEMARK OFFICE
CERTIFICATE OF CORRECTION

PATENT NO. : 6,620,798 B1
DATED : September 16, 2003
INVENTOR(S) : Russell Jaffe It is certified that error appears in the above-identified patent and that said Letters Patent is hereby corrected as shown below:

<u>Column 6,</u>
Line 34, change "1" to -- 0.1 --.

Signed and Sealed this

Twenty-seventh Day of January, 2004

JON W. DUDAS
*Acting Director of the United States Patent and Trademark Office*